United States Patent [19]

Felder et al.

[11] 4,001,323
[45] Jan. 4, 1977

[54] WATER-SOLUBLE, NON-IONIZING HYDROXY-CONTAINING AMIDE DERIVATIVES OF 2,4,6-TRIIODO-ISOPHTHALIC ACID

[75] Inventors: Ernst Felder, Riva S. Vitale, Switzerland; David E. Pitre, Milan, Italy

[73] Assignee: Savac AG, Chur, Switzerland

[22] Filed: Nov. 24, 1975

[21] Appl. No.: 634,836

[30] Foreign Application Priority Data

Dec. 13, 1974  Switzerland ............... 16588/74

[52] U.S. Cl. .................. 260/559 A; 260/562 A; 424/5; 260/558 A; 260/558 D
[51] Int. Cl.² ............... C07C 103/26; A61K 29/02
[58] Field of Search ............ 260/559 A; 424/5

[56] References Cited
UNITED STATES PATENTS

| | | | |
|---|---|---|---|
| 3,701,771 | 10/1972 | Almen et al. | 424/5 X |
| 3,867,431 | 2/1975 | Felder et al. | 424/5 X |
| 3,886,203 | 5/1975 | Felder et al. | 260/518 A X |
| 3,910,989 | 10/1975 | Felder et al. | 424/5 X |
| 3,912,776 | 10/1975 | Pfeiffer et al. | 424/5 X |

*Primary Examiner*—Daniel E. Wyman
*Assistant Examiner*—Thomas A. Waltz
*Attorney, Agent, or Firm*—Hans Berman

[57] ABSTRACT

Compounds of the formula

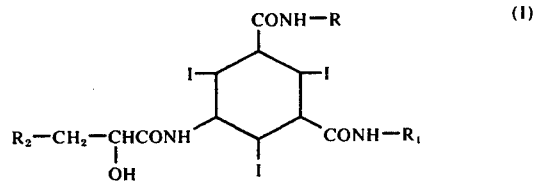

wherein R and $R_1$ are 1,3-dihydroxyisopropyl or 2,3-dihydroxypropyl, and $R_2$ is hydrogen or hydroxyl, are readily water-soluble and of sufficiently low toxicity for use as radiopaque materials in the radiography of body cavities as in urography, angiography, ventriculography, and myelography.

3 Claims, No Drawings

WATER-SOLUBLE, NON-IONIZING HYDROXY-CONTAINING AMIDE DERIVATIVES OF 2,4,6-TRIIODO-ISOPHTHALIC ACID

This invention relates to X-ray contrast agents, and particularly to compounds which are derivatives of 2,4,6-triiodo-isophthalic acid really soluble in water, non-ionized in solution, and sufficiently non-toxic for use as radiopaque components in X-ray contrast compositions, to such compositions, and to methods of preparing the compounds.

It has been found that compounds of the formula

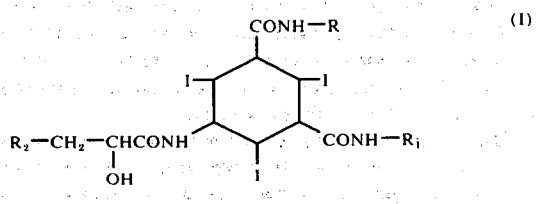

wherein R and $R_1$ are 1,3-dihydroxyisopropyl or 2,3-dihydroxypropyl, and $R_2$ is hydrogen or hydroxyl, combine the desired properties in a favorable manner not heretofore available.

5-Acylamino-2,4,6-triiodo-isophthalic acid diamides have been recommended heretofore as X-ray contrast agents (Swiss Pat. No. 544,551). If their carbamide groups are derived from secondary amines, they are obtained as mixtures of several isomers which are not capable of being separated. Yet, the use of compounds which are not absolutely pure and free from isomers is not available in human radiography. When the carbamide groups of the known compounds are derived from primary amines, the compounds are too poorly soluble in water to permit their use in aqueous contrast compositions A typical representative of radiopaque, known non-ionized, water soluble compounds is metrizamide (3-acetylamino-5-N-methyl-acetylamino-2,4,6-triiodo-benzoyl -glucosamine; U.S. Pat. No. 3,701,771). It is very soluble in water and is relatively non-toxic. However, it is difficult to prepare, and the mixture of isomers produced by all available methods of synthesis is practically unable of being resolved to pure, individual compounds. Its thermal stability is so low as to restrict its application.

The compounds of the invention are free from the shortcomings of the chemically related, known, radiopaque compounds. They are the first non-ionic 2,4,6-triiodobenzene derivatives which are readily soluble in water, but are free from contaminating isomers. Their solutions in pure water lack significant electric conductivity, an important feature in the radiography of the brain and of cavities filled with cerebrospinal fluid. The osmotic pressure of their solutions is very low so as to permit radiography of damaged kidneys. They are thermally more stable than chemically similar radiopaque materials available heretofore so as to permit sterilization of their solutions by heating. They are quickly excreted with the urine so as to make them applicable for urography. They are tolerated in intraperitoneal or intravenous application as well as any contrast agent in present clinical use. They are also well tolerated in intracarotideal, intracerebral, and intracisternal application.

The compounds of the invention contain one or more asymmetrical carbon atoms. While both the optically active and racemic forms are useful in aqueous contrast compositions, the optically active forms are more soluble in water than the racemates. The advantages of the compounds of the invention over the nearest state of the art and over many other known radiopaque compounds are thought to be due to the side chain R—CH$_2$—CHOH—CO— in the above formula.

The following Tables list the results of comparison tests between compounds of the invention and relevant known compounds. The compounds are identified in the Tables by capital letters as follows:

A: L-5-α-Hydroxypropionylamino-2,4,6triiodo-isophthalic acid di-(1,3-dihydroxyisopropylamide)
B: DL-5-α-Hydroxypropionylamino-2,4,6triiodo-isophthalic acid di-(1,3-dihydroxyisopropylamide)
C: L-5-α-Hydroxypropionylamino-2,4,6-triiodo-isophthalic acid di-(2,3-dihydroxypropylamide)
D: DL-5-α-Hydroxypropionylamino-2,4,6triiodo-isophthalic acid di-(2,3--dihydroxypropylamide)
E: 5-Acetylamino-2,4,6-triiodo-isophthalic acid di-(1,3-dihydroxisopropylamide)
F: 5-Acetylamino:2,4,6-triiodo-isophthalic acid di-(2,3-dihydroxypropylamide)
G: 5-Acetylamino-2,4,6-triiodo-isophthalic acid di-(N-methyl-2,3-dihydroxypropylamide)
H: 3-Acetylamino-5-N-methyl-acetylamino-2,4,6-triiodobenzoyl-glucosamine
I: Iodomethanesulfonic acid αγ-dihydroxyisopropylamide
K: 5,5'-Adipoyldiimino-bis-(2,4,6-triiodo-N-methyl-isophthalamic acid).

The compounds A to D according to the invention were prepared as shown in Examples Nos. 2 to 5 hereinbelow. The two Compounds E and F are chemically closely related to Compounds A to D. Compound F is known from U.S. Pat. No. 3,701,771, as are the Compounds G and H (metrizamide), the preferred compounds proposed in the patent. Compound I is the best compound of its type proposed in Swiss Pat. No. 550,003. Compound K (iocarmic acid) is typical of radiopaque compounds now in clinical use in the form of their salts for vasography and for the radiography of body cavities containing cerebrospinal fluid.

All tests were performed under closely controlled, identical conditions by methods commonly accepted in this art so that they are capable of quantitative comparison.

Table I lists solubilities in water in g/100 ml at 20°, 40°, and 60° C and $R_f$ values obtained by thin-layer chromatography of 200 μg on silica gel (F254) with solvent systems identified as follows:
- (a) Methylene chloride/methanol 10:3
- (a') Choroform/methanol25% aqu. ammonia 6:3:1
- (b) Ethyl acetate/ethanol/25% aqu. ammonia 15:7:6
- (b') Methylethylketone/glacial ac.ac.water 15:3:5

Where more than one $R_f$ value is listed for the same compound and the same solvent system, more than one spot was found in the chromatogram. $R_f$ values in brackets indicate minor ammounts. The listing of a single $R_f$ value indicates that only one spot was found.

Table II lists results of tests for toxicity and for secretion with the urine for Compounds A, G, H, I, and K. Because of their poor solubility. Compounds E and F could not be included in these tests. Toxicities are listed as value of LD$_{50}$ in mg iodine per kg body weight. Tests for intravenous (i.v.) intraperitoneal (i.p.), and intracerebral (i.cc.) toxicity were performed on mice. Test for intracisternal (i.ci.) toxicity were performed on rabbits, and tests for intracarotideal (i.ca.) toxicity on rats.

The solutions injected for i.v., i.p., i.ci., and i.ca. toxicity tests contained 400 mg I per ml. The rate of injection was 20 mg I per kg and minute for i.v. and i.ca. toxicity. In the tests for i.cc. toxicity, the injected volume was 5ml/kg, and the concentration was varied. Results of i.v. and i.p. toxicity tests were evaluated after 12 days, results of i.cc. and i.ca. toxicity tests after 48 hours.

Urinary secretion was determined on rabbits in percent excreted within three hours of the dosis of 200 mg I per kg administered intravenously.

TABLE I

| Comp'd | Solubility at °C | | | $R_f$ Value | |
|---|---|---|---|---|---|
| | 20 | 40 | 60 | | |
| A | 89 | 104 | 115 | (a) | 0.2 |
| | | | | (b) | 0.28 |
| B | 30 | 30 | 32 | (a') | 0.17 |
| C | 15.7 | 21 | 40 | (a) | 0.14 |
| | | | | (b) | 0.23 |
| D | 14 | 20 | 34 | (a') | 0.16 |
| | | | | (b') | 0.38 |
| E | 0.2 | | 0.5 | (a) | 0.28 |
| | | | | (b) | 0.43 |
| F | 0.5 | 0.8 | 1.5 | (a) | 0.16 |
| | | | | (b) | 0.16 |
| G | 55 | | | (a) | 0.19 |
| | | | | | 0.27 |
| | | | | | 0.34 |
| | | | | | 0.37 |
| | | | | (b) | 0.34 |
| | | | | | 0.4 |
| | | | | | 0.49 |
| H | abt. 80 | | | (a) | 0.3 |
| | | | | | (0.11) |
| | | | | | (0.36) |
| | | | | | (0.49) |
| | | | | | (0.64) |
| | | | | (b) | 0.19 |
| | | | | | 0.14 |
| | | | | | (0.24) |

TABLE II

| Comp'd | Toxicity, LD$_{50}$ mg I/kg | | | | | Urin'y Secr'n % |
|---|---|---|---|---|---|---|
| | i.v. | i.p. | i.cc. | i.ci. | i.ca. | |
| A | 21800 | 20000 | 1500 | 250 | 6500 | 77 |
| G | 15700 | | 820 | 81 | | |
| H | 10200*) | 4800 | 1400 | 100 | | 78 |
| I | 4700 | | 385 | 89 | | |
| K | 5500 | | 280 | 37 | 4000–5000 | 50 |

*)At the 170th Am. Chem. Soc. meeting, Chicago, August 1975, F.L. Weitl reported i.v. LD$_{50}$ in mice to be 23.8 g/kg or 11400 mg I per kg.

Aqueous solutions of Compound A containing 300 and 400 mg iodine respectively had viscosities of 8.95 and 40.6 c.p. at 20°, 4.70 and 16.1 c.p. at 37° C. A low viscosity facilitates injection.

For a comparison of thermal stability, aqueous solutions of Compounds A and H containing 400 mg I per ml where heated under nitrogen at 120° C. pH, iodide ion concentration and appearance were determined initially, after 30 minutes and after 15 hours. The results are shown in Table III.

TABLE III

| | Compound A | Compound H |
|---|---|---|
| pH, initial | 7.43 | 6.54 |
| 30 min. | 7.29 | 6.45 |
| 15 hrs. | 5.15 | 2.65 |
| mg I⁻ per ml, in'l | 0.15 | 0.66 |

TABLE III-continued

| | Compound A | Compound H |
|---|---|---|
| 30 min. | 0.3 | 1.71 |
| 15 hrs. | 1.8 | 40.60 |
| Appearance, in'l | (1) (2) | (1) |
| 30 min. | (1) (2) | (3) |
| 15 hrs. | (1) (3) | (4) |

(1) Clear solution
(2) Colorless
(3) Slightly colored
(4) Brown suspension, black sediment The iodine atoms in compounds of Formula (I) may be replaced by radioactive iodine by known methods, but the compounds may also be prepared from starting materials containing radioactive iodine as a tracer. The radioactive compounds of the invention are useful for special diagnostic procedures such as scintiphotography, and for special function tests.

The compounds of the invention are eminently suitable for use in most fields of application in which water soluble radiopaque compounds are necessary, such as vasography, urography, arthrography, and for the visualization of body cavities containing cerebrospinal fluid. When formulated with addition agents which increase the viscosity of the aqueous solutions, they may be employed to advantage for bronchography and hysterosalpingography.

They are superior to contrast agents in present clinical use in vasography and urography by the osmotic pressure of their solutions which is approximately one half of the osmotic pressure of known contrast agent solutions. They greatly reduce the problems in intravenous pyelography, particularly in patients of impaired kidney function and in dehydrated patients.

The radiopaque compounds of the invention are particularly useful as active ingredients of aqueous compositions for visualization of the cardiovascularsystem and for cerebral angiography. Because of their non-ionic nature, they are suited for visualization of body cavities containing spinocerebral liquor such as in radiculography, ventriculography, and myelography Aqueous compositions for the applications indicated above may be formulated to contain a single compound of the invention, or more than one compound of the invention, if the individual compounds are very pure.

The compounds of the invention which are optically active, and particularly the L-enantiomorphs which are prepared from derivatives of L-lactic acid, are preferred. They are more soluble and prepared from materials more easily available than the derivatives of DL-lactic acid or of glyceric acid. Derivatives of D-lactic acid are much more costly. The D-enantiomorphs of the compounds of the invention have not been found to offer advantages over the L-enantiomorphs, and none can be expected.

The preferred compound of the invention is 5-α-hydroxypropionylamino-2,4,6-triiodo-isophthalic acid di-(1,3-dihydroxyisopropylamide) for reasons obvious from Table 1, and particularly the L-enantiomorph (Compound A).

The radiopaque compositions of the invention are aqueous solutions containing 15 g and more of the compounds per 100 ml, equivalent to 60 to approximately 500 mg iodine per ml. The more concentrated solutions are generally preferred, and they are applied in a manner generally known and selected according to the body cavity which it is intended to visualize. In vasography, the solutions are injected or infused into the vessels, particularly the blood vessels. Intravenous injection is resorted to in urography. For myelography and radiculography, the solutions are instilled after lumbar or suboccipital puncture. The amounts of solution necessary generally are 5 to 15 ml for myelography, 3 to 5 ml for radiculography, and 1 to 2 ml in ventriculography.

The X-ray contrast compositions containing the compounds of the invention as active ingredients are prepared in a very simple manner since no salt-forming or solubilizing ingredients are needed. Any one of the pure 2,4,6-triiodoisophthalic acid diamides mentioned in the following Examples 2 to 8 may be dissolved under sterile conditions in the desired amount of double-distilled water, and the solution so obtained is ready to be received in vials and sterilized. The compounds are not decomposed at sterilizing temperatures during the usual sterilizing periods (30 minutes at 120° C or 60 minutes at 100° C).

The following Examples are further illustrative of this invention. All solubility values are in grams per 100 ml unless stated otherwise.

EXAMPLE 1

400 g (0.72 Mole) 5-amino-2,4,6-triiodo-isophthalic acid was added to 200 ml thionyl chloride, the mixture was stirred at a boil for six hours, and the resulting solution was evaporated. The residue was dissolved in anhydrous ethyl acetate, and the solution was again evaporated to dryness. The solid material was dissolved in 4000 ml ethyl acetate, and the solution was stirred into an ice-cold solution of 500 g sodium chloride and 200 g sodium bicarbonate in 2.5 liters water. The organic phase was separated from the aqueous solution, washed with aqueous sodium chloride solution, dried by contact with anhydrous calcium chloride, and evaporated to dryness.

The residue of 420 g 5-amino-2,4,6-triiodo-isophthalyl chloride (97.5% yield) had a melting point above 300° C when recrystallized from toluene.

300 g (0.503 mole) 5-amino-2,4,6-triiodo-isophthalyl chloride was dissolved in 1200 ml dimethylacetamide, and 187 g (1.26 mole) L-2-acetoxypropionyl chloride was added dropwise to the solution at 3° 14 5° C with agitation. The mixture was permitted to stand overnight at ambient temperature and was then evaporated in a vacuum to approximately 400 ml. The oily residue was stirred into ice water to precipitate 353 g crystalline L-5-(α-acetoxypropionylamino)2,4,6-triiodo-isophthalyl choride (98% yield) which was purified by suspension in warm chloroform free from alcohol.

The purified intermediate melted at 219° – 220° C, had a specific rotation $[\alpha]_D^{20} = -13.0°$ (c = 5, in CHCl$_3$). Its chlorine content of 10.2%, as determined by analysis, was in good agreement with the calculated value of 9.98% for $C_{13}H_8Cl_2I_3NO_5$. An R$_f$ value of 0.46 was determined by thin layer chromatography on silica gel with benzene-methanol mixture 10:2, and development with chlorine vapor and by spraying with a solution of 4,4′-diamino-2,2′-dimethyldiphenyl and a little potassium iodide in aqueous acetic acid.

EXAMPLE 2

28.4 g (0.04 Mole) of the intermediate prepared in Example 1 was dissolved in 150 ml dimethylacetamide, and 15 g (0.08 mole) tributylamine was added. The mixture was heated to 50° C, and 9.1 g (0.1 mole) 1,3-dihydroxyisopropylamine (2-amino-1,3-propanediol) dissolved in 80 ml dimethylacetamide was added drop by drop. The reaction went to completion within a few hours, and the reaction mixture was evaporated to dryness in a vacuum. The oily residue was added to 350 ml methylene chloride with vigorous agitation, and the resulting precipitate was filtered off and purified by repeated suspension in warm methylene chloride.

L-5-α-Acetoxypropionylamino-2,4,6,-triiodo-isophthalic acid di-(1,3-dihydroxyisopropylamide) was obtained in a yield of 30 g (92%) and melted at 185° – 187° C. It was dissolved in water, and the solution was decolorized with active carbon, adjusted to pH 11 with concentrated sodium hydroxide solution, heated to 40° C, and mixed with additional NaOH solution until the pH stabilized, indicating the complete saponification of the acetoxy groups.

Sequential contact with cation and anion exchange resins caused the removal of salts from the saponification mixture, and the deionized solution was evaporated to dryness. The residue was further purified by recrystallization from ethanol.

L-5-α-Hydroxypropionylamino-2,4,6-triiodo-isophthalic acid di-(1,3-dihydroxyisopropylamide) (Compound A) was obtained in a yield of 20 g (65%), decomposed at about 300° C without melting, had a specific rotation $[\alpha]_D^{20} = -2.01°$ (c = 10, in water), and gave an R$_f$ value of 0.2 in a thin layer chromatogram on silica gel with a methylene chloride - methanol mixture 10:3.

Elementary analysis showed 26.37% C and 48.79% I against respective values of 26.27% and 48.99% calculated for $C_{17}H_{22}I_3N_3O_8$.

Compound A is very readily soluble in water. 10 Ml of a solution containing 10 g Compound A was stored several days at 4° C, whereby only 2.3 g of the compound was precipitated. Solubility in methanol also is practically unlimited. At room temperature, solubility in ethanol is about 10 g/100 ml, but Compound A is miscible with boiling ethanol.

Compound A is also obtained when 1,3-dihydroxyisopropylamine in the above reaction is replaced by the ketal of the amine with acetone (5-amino-2,2-dimethyl-1,3-dioxane, Swiss patent No. 550,003) in an equivalent amount. The primary reaction product is L-5-(α-acetoxypropionylamino)-2,4,6-triiodo-isophthalic acid di-(2,2-dimethyl-1,3-dioxan-5-yl-amide) which is purified by recrystallization from isopropanol. The ketal groups are split at once by treatment with a little 0.1 N hydrochloric acid, and the solid material dissolves. Saponification of the acetoxy group in position 5-α as described above, yields the desired compound.

EXAMPLE 3

DL-5-α-Acetoxypropionylamino-2,4,6-triiodo-isophtalyl chloride was prepared from DL-2-acetoxypropionyl chloride by the method of Example 1 and melted at 210° C.

The last-mentioned intermediate was reacted in an amount of 70.9 g (0.1 mole) with 56.5 g (0.62 mole) 2-amino-1,3-propanediol. Work-up of the reaction mixture as in Example 2 yielded 56.5 g (73.5%) DL-5-α-hydroxypropionylamino2,4,6-triiodo-isophthalic acid di-(1,3-dihydroxyisopropylamide) (Compound B)

which was recrystallized from aqueous ethanol and melted with decomposition above 300° C. It gave an $R_f$ value of 0.17 by thin layer chromatography on silica gel with a solvent mixture of chloroform, methanol, and 25% aqueous ammonia 6:3:1 and was identified by its iodine content of 48.97%.

Compound B dissolves in water at 20° C at a rate of 30 g per 100 ml.

EXAMPLE 4

34.6 g (0.049 Mole) 5-L-α-acetoxypropionylamino)-2,4,6-triiodo-isophthalyl choride and 18 g (0.098 mole) tributylamine were dissolved in 200 ml dimethylacetamide, 13.2 g (0.145 mole) racemic 2,3-dihydroxypropylamine was added drop by drop, and the reaction was permitted to go to completion, whereupon the reaction mixture was worked up as in Example 2. Saponification of the reaction product with sodium hydroxide and deionization of the saponification mixture yielded 28.5 g (73.5%) crude L-5-α-hydroxypropionylamino-2,4,6-triiodo-isophthalic acid di-(DL-2,3-dihydroxypropyl-amide) (Compound C) which can be purified by recrystallization from very little water or preferably from aqueous ethanol.

The purified product decomposes at 281° – 283° C, has a specific rotation $[\alpha]_D^{20} = -0.78°$ (c = 10, in water), and gives an $R_f$ value of 0.23 in a thin layer chromatogram with ethyl acetate/ethanol/aqueous 25% ammonia 15:7:6. It was identified by its carbon content of 26.14% and iodine content of 48.96%. Compound C is very easily soluble in water, somewhat less soluble in ethanol.

It was also prepared by substituting an equivalent amount of 4-aminoethyl-2,2-dimethyl-1,3-dioxolane for the 2,3-dihydroxypropylamine indicated above, as in Example 2, and by further processing the 5-α-acetoxypropionylamino-2,4,6-triiodo-isophthalic acid di-(2,2-dimethyl-1,3-dioxolan-4-yl-methylamide) which is practically insoluble in water and readily purified due to this property.

EXAMPLE 5

85 g (0.12 Mole) DL-5-α-acetoxypropionylamino-2,4,6-triiodo-isophthalyl chloride was reacted with 32.8 g (0.36 mole) racemic 1-amino-2,3-propanediol, and the reaction mixture was worked up as in Example 4. 5-DL-α-Hydroxypropionylamino-2,4,6-triiodo-isophthalic acid di-(DL-2,3-dihydroxypropylamide) (Compound D) was obtained in an amount of 62.7 g 68% yield), and melted at 285° – 286° C (decomp.) when recrystallized from a little water. Its thin chromatogram gave an $R_f$ value of 0.16 with chloroform/methanol/25% aqueous ammonia 6:3:1. Compound D was identified by its iodine content of 48.86%.

All three asymmetric carbon atoms in Compound D are in the racemic form, and the compound is somewhat less soluble than Compound C which was prepared from a derivative of optically active lactic acid. The solubility of Compound D in water was found to be 14 g/100 ml at 20° C, 20 g/100 ml at 40° C, and 34 g/100 ml at 60° C. The enantiomorphs in which all three carbon atoms are in the optically active state were prepared in the manner of Example 4, the D- and L-forms of 1-amino-2,3-propanediol being substituted for the racemate. The compounds so obtained were practically infinitely soluble in water.

EXAMPLE 6

A solution of 6.84 g (0.075 mole) 1,3-dihydroxyisopropylamine in 60 ml dimethylacetamide was added dropwise to 20.5 g (0.03 mole) PL-5-α,β-diacetoxypropionylamino-2,4,6-triiodo-isophthalyl chloride and 11.1 g (0.06 mole) tributylamine in 120 ml dimethylacetamide at 2° – 5° C. The mixture was left to stand 22 hours at room temperature, was thereafter kept 3 hours at 45° C, and was ultimately evaporated to dryness in a vacuum. The oily residue was stirred into 300 ml methylene chloride, and the resulting precipitate was filtered off and purified by suspension in warm methylene chloride. 20.5 g DL-5-α,βDiacetoxypropionylamino-2,4,6-triiodo-isophthalic acid di-(1,3-dihydroxyisopropylamide) was recovered in a yield of 20.5 g (77.9%). It melted at 203° – 209° C after sintering at 94° – 148° C.

An aqueous solution of the compound was decolorized with active carbon and adjusted with concentrated sodium hydroxide solution to pH 12 – 12.5. It was then heated to 40° C, and more NaOH was added until the pH remained constant. The saponification mixture was then deionized by passage over cation and anion exchange resins, and evaporated to dryness.

The residue was recrystallized from aqueous methanol and consisted of 11.6 g DL-5-α,β-dihydroxypropionylamino-2,4,6-triiodo-isophtalic acid di-(1,3-dihydroxyisopropylamide) (62.5% yield). It sintered and melted at 210° – 230° C and decomposed at 260° C. It gave an $R_f$ value of 0.15 by thin layer chromatography on silica gel with chloroform/methanol/aqueous 25% ammonia 6:3:1. It was identified by elementary analysis for carbon and iodine which yielded values of 25.70% C and 48.29% I against 25.74% and 48.00% respectively calculated for $C_{17}H_{22}I_3N_3O_9$. It has good solubility in warm water and tends to form supersaturated solutions which are stable for several hours at 37° C.

5-α,β-dihydroxypropionylamino-2,4,6-triiodo-isophthalic acid di-(2,3-dihydroxypropylamide) was prepared in an analogous manner.

The DL-5-diacetoxypropionylamino-2,4,6-triiodo-isophthalyl chloride employed as a starting material was prepared by adding 52.2 g (0.25 mole) 2,3-diacetoxypropionyl chloride (Browning et al. Proc. Royal Soc. B 110, 375) drop by drop to 59.6 g (0.10 mole) 5-amino-2,4,6-triiodo-isophthalyl chloride in 250 ml dimethylacetamide at room temperature, storing the mixture at room temperature for 5 days, and evaporating it to dryness. The residue was washed repeatedly with water, and was purified by chromatography on 15 times its weight of silica gel with chloroform/ethyl acetate 9:1.

The pure compound obtained in a yield of 49.4 g (65%) melted at 189° – 190° C. It contained 23.58% C and 49.67% I as compared to values of 23.46% and 49.58% calculated for $C_{15}H_{10}Cl_2I_3NO_7$. A thin layer chromatogram with chloroform/ethyl acetate/hexane 1:1:1 gave an $R_f$ value of 0.7.

EXAMPLE 7

47.9 g (0.2 Mole) dimethyl 5-nitro-isophthalate was mixed with 22.8 g (0.25 mole) 1,3-dihydroxyisopropylamine (serinol), and the mixture was stirred for five hours at 140° – 150° C, whereby methanol was distilled off. The residue was cooled to room temperature, taken up in a little water, and stored several hours at 0° C. 57.2 g 5-nitro-isophthalic acid di-(1,3-dihydroxyisopropylamide) was recovered as an intermediate by filtration and drying. It melted at 194° C, and thin layer chromatograms gave $R_f$ values of 0.26 with chloroform/methanol/25% aqueous ammonia 6:3:1 and 0.67 with methylethylketone/glacial acetic acid/water 15:3:5.

57.1 g Intermediate was dissolved in 250 ml ethanol at slightly elevated temperature and hydrogenated in the presence of 5 g 10% palladium-carbon catalyst. After removal of the catalyst, the hydrogenation mixture was evaporated to dryness, and the residue was dissolved in a mixture of 1 liter water and 20 ml concentrated hydrochloric acid. 305 ml 1 N $KICl_2$ solution was added dropwise at 30° – 50° C with vigorous stirring, and stirring was continued after the addition for approximately 17 hours at 50° – 60° C. Upon cooling, 5-amino-2,4,6-triiodo-isophthalic acid di-(1,3-dihydroxyisopropylamide) was filtered off, washed with dilute sodium bisulfite solution and water, and then dried. The recovered compound weighed 84.6 g (75% yield, based on the above intermediate), melted at 275° C (decomp.), and gave $R_f$ values of 0.22 and 0.58 in respective thin layer chromatagrams with the above two solvent systems.

60 g (About 0.4 mole) L-2-acetoxypropionyl chloride was added dropwise to 70.5 g (0.1 mole) 5-amino-2,4,6-triiodoisophthalic acid di-(1,3-dihydroxyisopropylamide) in 250 ml dimethylacetamide with stirring at 0° – 5° C. The mixture was stored overnight at room temperature and then evaporated to dryness in a vacuum. The residue was dissolved in water, decolorized with active carbon, and saponified at 40° C and pH 11 by repeatedly replenished sodium hydroxide as described above. The saponification solution was deionized and evaporated to dryness. The residue of crude Compound A was further purified by filtration of its solution over active alumina, and ultimately recrystallized from a small amount of ethanol.

The pure compound was identified by its melting point, specific optical rotation, and iodine content.

EXAMPLE 8

Compound A was also prepared from 9.1 g (0.1 mole) 1,3-dihydroxyisopropylamine (serinol) which was added with stirring at 50° C to 23.83 g (0.04 mole) 5-amino-2,4,6-triiodo-isophthalyl chloride and 15 g (0.08 mole) tributylamine in 170 ml dimethylacetamide. The mixture was evaporated to dryness after a few hours, the residue of 5-amino-2,4,6-triiodoisophthalic acid di-(1,3-dihydroxyisopropylamide) was purified by stirring in methylene chloride, and the purified intermediate (19 g, m.p. 274° C, decomp.) was reacted with 15 g L-acetoxypropionyl chloride in the manner of Example 7, and L-5-α-hydroxypropionylamino-2,4,6-triiodo-isophthalic acid di-(1,3-dihydroxy-isopropylamide) was obtained by saponification and further work-up as in the preceding Examples in an amount of 14.1 g.

EXAMPLE 9

82.5 g L-5-α-Hydroxypropionylamino-2,4,6-triiodo-isophthalic acid di-(1,3-dihydroxyisopropylamide) was dissolved in a small amount of bi-distilled water at 37° C under a nitrogen blanket. The solution was adjusted to pH 7 by adding 0.24 g sodium bicarbonate, filtered through a filter of a pore diameter of 0.22 m$\mu$, diluted with bi-distilled water to 100 ml, transferred to multiple-puncture vials of 10 and 20 ml capacity under sterile conditions, and sterilized. It contained 400 mg iodine per ml.

An injectable solution containing 500 mg iodine per ml was prepared in an analogous manner from 82 g Compound A, 20.5 g Compound C, 0.4 g sodium bicarbonate, and 0.02 g disodium phosphate of EDTA and enough water to make 100 ml.

What is claimed is:
1. A compound of the formula

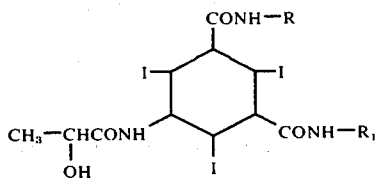

wherein R and $R_1$ are members of the group consisting of 1,3-dihydroxyisopropyl and 2,3-dihydroxypropyl.
2. A compound as set forth in claim 1, wherein each of said R and $R_1$ is 1,3-dihydroxyisopropyl.
3. A compound as set forth in claim 2, which is optically active.

* * * * *

UNITED STATES PATENT AND TRADEMARK OFFICE
CERTIFICATE OF CORRECTION

PATENT NO. : 4,001,323

DATED : January 4, 1977

INVENTOR(S) : Ernst Felder et al.

It is certified that error appears in the above-identified patent and that said Letters Patent is hereby corrected as shown below:

In the Abstract of the patent [57], and in column 1 the formula of the compound should appear as follows:

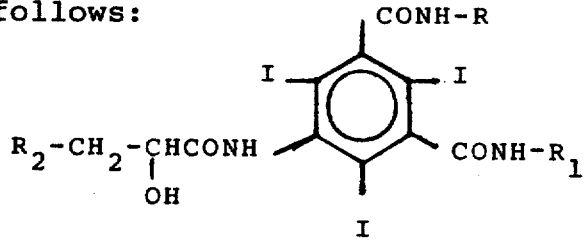

in column 10, the formula of the compound should appear as follows:

UNITED STATES PATENT AND TRADEMARK OFFICE
CERTIFICATE OF CORRECTION

PATENT NO. : 4,001,323
DATED : January 4, 1977
INVENTOR(S) : Ernst Felder et al

It is certified that error appears in the above-identified patent and that said Letters Patent is hereby corrected as shown below:

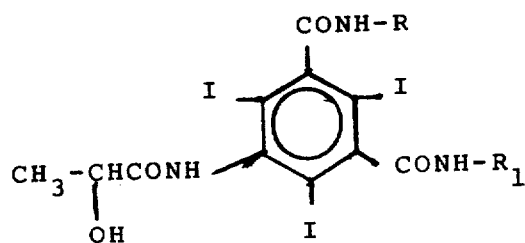

Signed and Sealed this

Sixteenth Day of September 1986

[SEAL]

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,001,323

Dated         : January 4, 1977

Inventor(s)   : Ernst Felder, et al

Patent Owner  : Bracco Industria
                Chimica S.p.A.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Nineteenth day of December 1986.

Donald J. Quigg

Assistant Secretary and Commissioner of Patents and Trademarks